United States Patent
Culha (10) Patent No.: US 10,967,064 B2
(45) Date of Patent: Apr. 6, 2021

(54) PREPARATION METHOD FOR A DNA ORIGAMI BASED CARRIER SYSTEM

(71) Applicant: YEDITEPE UNIVERSITESI, Istanbul (TR)

(72) Inventor: Mustafa Culha, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 360 days.

(21) Appl. No.: 16/072,176

(22) PCT Filed: Jan. 22, 2016

(86) PCT No.: PCT/TR2016/050016
§ 371 (c)(1),
(2) Date: Jul. 23, 2018

(87) PCT Pub. No.: WO2017/127033
PCT Pub. Date: Jul. 27, 2017

(65) Prior Publication Data
US 2019/0030173 A1    Jan. 31, 2019

(51) Int. Cl.
| | |
|---|---|
| A61K 47/54 | (2017.01) |
| A61K 9/51 | (2006.01) |
| A61K 35/00 | (2006.01) |
| C12N 15/10 | (2006.01) |
| C12N 15/11 | (2006.01) |
| A61P 35/00 | (2006.01) |
| B82Y 5/00 | (2011.01) |

(52) U.S. Cl.
CPC ............ *A61K 47/549* (2017.08); *A61K 9/51* (2013.01); *A61P 35/00* (2018.01); *C12N 15/10* (2013.01); *C12N 15/11* (2013.01); *C12N 15/111* (2013.01); *B82Y 5/00* (2013.01); *C12N 2320/32* (2013.01)

(58) Field of Classification Search
None
See application file for complete search history.

(56) References Cited

U.S. PATENT DOCUMENTS

2007/0117109 A1    5/2007 Rothemund

FOREIGN PATENT DOCUMENTS

| WO | 2008147526 A1 | 12/2008 |
| WO | 2010017264 A2 | 2/2010 |
| WO | 2014153394 A1 | 9/2014 |

OTHER PUBLICATIONS

Pinar Akkus Sut, et al.:"Research article—Lactose-modified DNA tile nanostructures as drug carriers", Researchgate, Jan. 25, 2016 (Jan. 25, 2016), pp. 1-46, XP002761051, Retrieved from the Internet: URL: http://www.tandfonline.com/doi/full/10.3109/1061186X.2016.1144059?scroll=top&needAccess=true [retrieved on Aug. 24, 2016] the whole document Published in the Journal of Drug Targeting,vol. 24, 2016—Issue 8, pp. 709-719.

Jiang Qiao et al:"DNA origami as a carrier for circumvention of drug resistance.", Journal of the American Chemical Society, vol. 134, No. 32, Aug. 15, 2012 (Aug. 15, 2012), pp. 13396-13403, XP002761052,ISSN:1520-5126 cited in the application the whole document.

Yong-Xing Zhao et al:"DNA Origami Delivery System for Cancer Therapy with Tunable Release Properties", ACS Nano, vol. 6, No. 10, Oct. 23, 2012 (Oct. 23, 2012), pp. 8684-8691, XP055065125, ISSN: 1936-0851, DOI:10.1021/nn3022662 cited in the application the whole document.

Ilknur Sur et al:"Interaction of multi-functional silver nanoparticles with living cells", Nanotechnology,IOP,Bistol,GB,vol. 21,No. 17,175104, Apr. 30, 2010 (Apr. 30, 2010), XP020174830,ISSN 0957-4484 the whole document.

Microsugar Chang et al:"Aptamer-Conjugated DNA Icosahedral Nanoparticles as a Carrier of Doxorubicin for Cancer Therapy",ACS Nano, vol. 5, No. 8, Aug. 23, 2011 (Aug. 23, 2011), pp. 6156-6163,XP055130736, ISSN 1936-0851, DOI:10.1021/nn200693a cited in the application the whole document.

Pal Suchetan et al:"DNA-origami-directed self-assembly of discrete silver-nanoparticle architectures.", Angewandte Chemie (International Edition in English) Apr. 1, 2010, vol. 49, No. 15, Apr. 1, 2020 (Apr. 1, 2010), pp. 2700-2704, XP002761053, ISSN 1521-3773 the whole document.

Stearns Linda A et al:"Template-directed nucleation and growth of inorganic nanoparticles on DNA scaffolds.", Angewandte Chemie (International Edition in English), vol. 48, No. 45, Sep. 30, 2009 (Sep. 30, 2009), pp. 8494-8496, XP002761054,ISSN 1521-3773 the whole document.

Bryan Wei et al:"Complex shapes self-assembled from single-stranded DNA tiles", Nature, vol. 485, No. 7400, May 30, 2012 (May 30, 2012), pp. 623-626, XP055082868, ISSN 0028-0836, DOI:10.1038/nature11075 the whole document.

Shawn M Douglas et al:"Self-assembly of DNA into nanoscale three-dimensional shapes", Nature, Nature Publishing Group, United Kingdom, vol. 459, No. 7245, May 21, 2009 (May 21, 2009), pp. 414-418, XP002690757,ISSN 0028-0836, DOI: 10.1038/NATURE08016 the whole document.

Um S H et al:"Enzyme-catalysed assembly of DNA hydrogel", Nature Materials, Nature Publishing Group, GB, vol. 5, No. 10, Oct. 1, 2006 (Oct. 1, 2006), pp. 797-801, XP002692004, ISSN: 1476-1122, DOI: 10.1038/NMAT1741 [retrieved on Sep. 24, 2006] the whole document.

(Continued)

*Primary Examiner* — Robert M Kelly
(74) *Attorney, Agent, or Firm* — Bayramoglu Law Offices LLC (57) ABSTRACT

The present invention provides a preparation method for a DNA origami based carrier, which essentially comprises the steps of performing multi-functional DNA origami based nanocarrier preparation.

7 Claims, 9 Drawing Sheets
Specification includes a Sequence Listing.

(56) References Cited

OTHER PUBLICATIONS

Yu He et al:"Hierarchical self-assembly of DNA into symmetric supramolecular polyhedra", Nature, Nature Publishing Group, United Kingdom, vol. 452, No. 7184, Mar. 13, 2008 (Mar. 13, 2008), pp. 198-201, XP002692005,ISSN 1476-4687, DOI: 10.1038/NATURE06597 the whole document.

SEQUENCE LISTING

```
<160> NUMBER OF SEQ ID NOS: 9

<210> SEQ ID NO 1
<211> LENGTH: 140
<212> TYPE: DNA
<213> ORGANISM: Artificial Sequence
<220> FEATURE:
<223> OTHER INFORMATION: Oligonucleotide 1

<400> SEQUENCE: 1
aggcaccatc gtaggaaaat ctgcgtcagc tctccgtaca ccagtgcttc catgcgaagt      60
aaaacgttcc gatcaccaac ggagtaaaac gatctaactg ataactagca cctctgctca     120
cgtgaggagt aaaacttgcc                                                  140
```

-continued

```
<210> SEQ ID NO 2
<211> LENGTH: 54
<212> TYPE: DNA
<213> ORGANISM: Artificial Sequence
<220> FEATURE:
<223> OTHER INFORMATION: Oligonucleotide 2

<400> SEQUENCE: 2
ataccggagg cttcctgtac ggagagctga cgcagaccta cgatggacac gccg        54

<210> SEQ ID NO 3
<211> LENGTH: 54
<212> TYPE: DNA
<213> ORGANISM: Artificial Sequence
<220> FEATURE:
<223> OTHER INFORMATION: Oligonucleotide 3

<400> SEQUENCE: 3
atgcaacctg cctggcaaga ctcctcacgt gagcagagga ctactcatcc gtta        54

<210> SEQ ID NO 4
<211> LENGTH: 54
<212> TYPE: DNA
<213> ORGANISM: Artificial Sequence
<220> FEATURE:
<223> OTHER INFORMATION: Oligonucleotide 4

<400> SEQUENCE: 4
tttccgactg agccctgcta gttatcagtt agatcgactc cgttggacga acag        54

<210> SEQ ID NO 5
<211> LENGTH: 54
<212> TYPE: DNA
<213> ORGANISM: Artificial Sequence
<220> FEATURE:
<223> OTHER INFORMATION: Oligonucleotide 5

<400> SEQUENCE: 5
atagcgcctg atcggaacga cttcgcatgg aagcactgga ccgttctacc gatt        54

<210> SEQ ID NO 6
<211> LENGTH: 40
<212> TYPE: DNA
<213> ORGANISM: Artificial Sequence
<220> FEATURE:
<223> OTHER INFORMATION: Oligonucleotide 6

<400> SEQUENCE: 6
ctcgcaatcg gtagaacggt ggaagcctcc ggtatgcatg                        40

<210> SEQ ID NO 7
<211> LENGTH: 36
<212> TYPE: DNA
<213> ORGANISM: Artificial Sequence
<220> FEATURE:
<223> OTHER INFORMATION: Oligonucleotide 7

<400> SEQUENCE: 7
aaaaaaaaaa cggcgtgtgg ttgcataaaa aaaaaa                            36

<210> SEQ ID NO 8
<211> LENGTH: 40
<212> TYPE: DNA
<213> ORGANISM: Artificial Sequence
<220> FEATURE:
<223> OTHER INFORMATION: Oligonucleotide 8
```

```
<400> SEQUENCE: 8
cgctataacg gatgagtagt gggctcagtc ggaaagagca                             40

<210> SEQ ID NO 9
<211> LENGTH: 36
<212> TYPE: DNA
<213> ORGANISM: Artificial Sequence
<220> FEATURE:
<223> OTHER INFORMATION: Oligonucleotide 9

<400> SEQUENCE: 9
aaaaaaaaaa ctgttcgtgg cgctataaaa aaaaaa                                36
```

PREPARATION METHOD FOR A DNA ORIGAMI BASED CARRIER SYSTEM

CROSS REFERENCE TO RELATED APPLICATIONS

This application is the national phase entry of International Application No. PCT/TR2016/050016, filed on Jan. 22, 2016, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named "GBAP151_sequence listing.txt", created on Dec. 11, 2020, and is 2,139 bytes in size.

TECHNICAL FIELD

The present invention relates to a new way to prepare multifunctional DNA origami based drug nano-carrier and -delivery vehicle.

BACKGROUND

Adenine-thymine and guanine-cytosine Watson-Crick hydrogen bonding allows the preparation of artificial 2D and 3D DNA based nanostructures. Using DNA and artificial oligonucleotides, molecular structures with different sizes and shapes can be constructed. Since the first report for the construction of DNA origami structure by Paul Rothemund, the preparation of many 2D and 3D structures using simple base pairing (or DNA hybridization) has been demonstrated. The first 2D DNA structure was designed by Winfree et al. using DNA tiles. In 1999, the first discrete 3D structures were reported by Seeman.

The DNA tiles are rectangular shaped DNA structures that contain multiple antiparallel DNA crossovers. The first developed DNA tiles were consisted of two DNA double helices with two crossovers, subsequently structures contain three double helices with four crossovers were developed. The DNA tiles are designed to include short and unpaired single stranded DNA strands, which allow the binding of another tile. Through these free regions, called sticky ends, the DNA tiles can be combined to create larger DNA structures or modified with different molecules for several applications.

Although the use of DNA brings several advantages such as biocompatibility and biodegradability, it also has some disadvantages such as inefficient cellular uptake. Cellular uptake is an important parameter that should be considered for use of DNA constructs in drug delivery applications. Therefore, a molecular moiety that may utilize this function can be introduced into the DNA construct. The use of the viral vectors, peptides, and liposomes was reported as carrier structures to increase the cellular uptake efficiency. Carbohydrates are a group of biomacromolecules that may serve for this goal as well. Sugar conjugates were reported to be as effective as commercial transfection agents. The transfection efficiencies of the lactosylated and α-glucosylated polylysine structures were found high as commercial transfection agents, lipofectamine and PEI.

Doxorubicin is typical anthracycline type drug molecule and it is commonly used as chemotherapeutic agents for the cancer treatments, more specifically for breast cancer treatment. It mainly induces apoptotic cell death in cancer cells. Beside cancer cells, doxorubicin also affects other cells and shows side effects on healthy cells. To reduce side effects of doxorubicin, the novel vehicles have always been investigated.

The first DNA based system investigated for doxorubicin delivery was an aptamer conjugated DNA icosa, which was used for killing the cancer cells. Triangular-shaped and tubular-shaped DNA origami structures were used as carriers of doxorubicin. The effect of doxorubicin intercalated triangular-shaped and tubular-shaped DNA origami structures was investigated on regular human breast adenocarcinoma cancer cells, MCF7, and doxorubicin resistant subline and overcome to doxorubicin resistance. The two 18-helix bundle nanotubes were evaluated as delivery systems for doxorubicin.

SUMMARY

Figure 10:
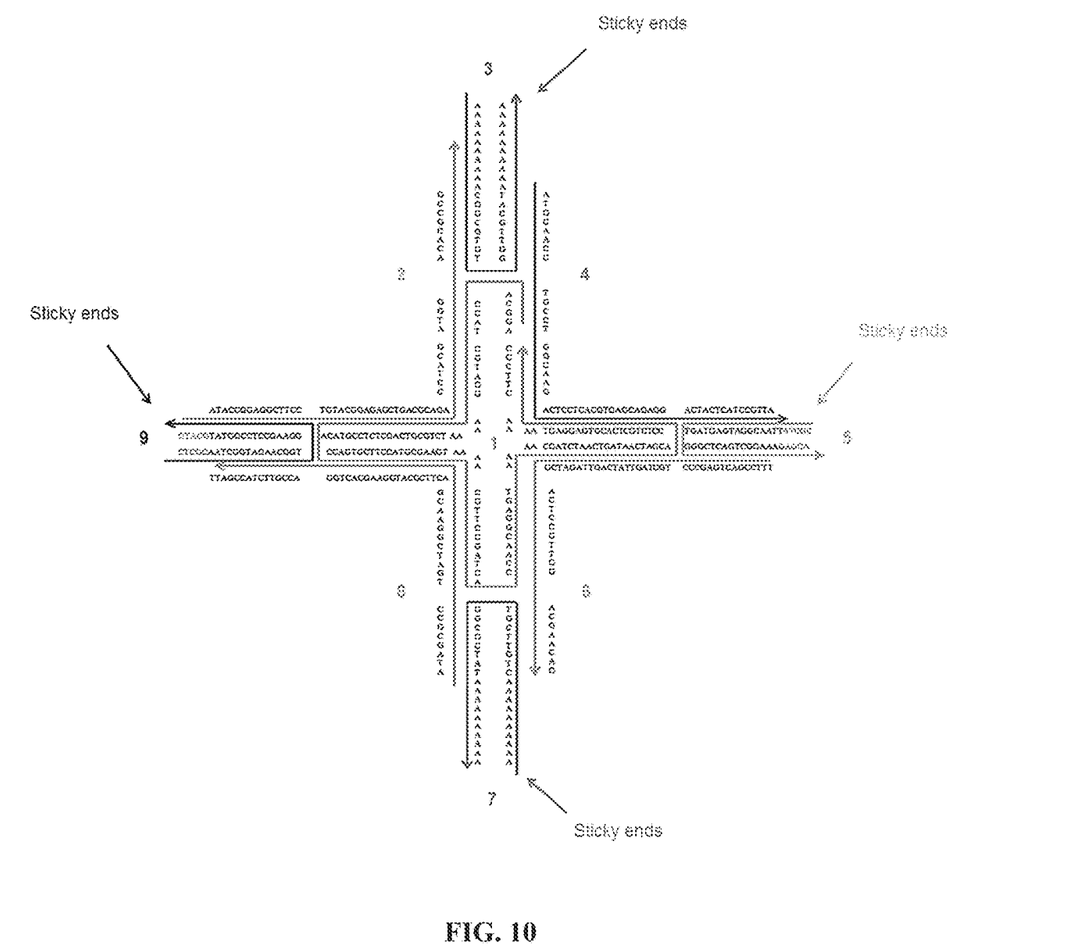
FIG. 10 is the schematic representation of proposed DNA origami structure with binding points of modified oligonucleotides.

The objective of the present invention is to prepare DNA origami based nano-carrier system, which can be used as drug delivery and targeting vehicle. A targeting agent such as a RGD peptide, a folic acid, or a sugar molecule can be bound through the sticky ends of the DNA origami purposely designed. FIG. 10 shows the proposed structure and binding points of the oligonucleotide modified agents including an RGD peptide, a folic acid, a sugar molecule and a drug molecule. A multifunctional DNA based nanocarrier system can be constructed by maintaining the basic origami tile structure and attaching the mentioned molecules to the oligonucleotides complementary to the sticky ends of the DNA origami structure.

A further objective of the present invention is to improve a cellular uptake of the DNA origami based carrier with modification using sugar (carbohydrate) molecules, lactose.

The present invention provides a preparing method for DNA origami based carrier, including the following steps:
1) preparing a DNA origami carrier:
    mixing complementary oligonucleotides in hybridization buffer,
    incubating the mixture in a water bath at 95° C.,
    slowly cooling the mixture from 95° C. to room temperature,
    characterizing the DNA origami carrier;
2) synthesizing lactose modified oligonucleotide:
    mixing lactose, 5'-aminohexyloligonucleotide and sodium cyanoborohydride in borate buffer (pH 8),
    stirring the mixture at room temperature for 12 hours,
    centrifuging the mixture to remove unreacted chemicals,
3) hybridizing lactose modified oligonucleotide to the DNA origami carrier:
    mixing the DNA origami structure and the lactosylated oligonucleotide in hybridization buffer at room temperature for 18 hours;
4) intercalating the doxorubicin into the DNA origami based carrier:
    mixing the hybridized DNA origami based carrier and doxorubicin in hybridization buffer,
    stirring the mixture at room temperature for 24 hours,
    centrifuging the mixture to collect the DNA origami-doxorubicin pellet.

In step 1), 2 μL of each complementary oligonucleotide from a 100 μM stock is added into the hybridization buffer TAE/$Mg^{2+}$ to have a final volume of 200 μL. The newly prepared DNA origami carrier is characterized using AFM, agarose gel electrophoresis and dynamic light scattering analysis.

In step 2), lactose (20 mM), 5'-aminohexyloligonucleotide (50 µM) and sodium cyanoborohydride (250 mM) are added into borate buffer (pH 8, 0.1 M) and incubated for 12 hours at 60° C. The reaction mixture is transferred into an ultracentrifuge column with 3000 MWCO and centrifuged for 45 minutes at 3800 rpm to remove unreacted chemicals. The reaction products are monitored with agarose gel electrophoresis. 2% agarose gel is prepared and run in 1×TAE buffer at 60 V for 90 minutes.

In step 3), 10 µL of the lactosylated oligonucleotide is hybridized into 30 µL of the DNA origami carrier by incubating them together at room temperature for 18 hours in a hybridization buffer (TAE/Mg$^{2+}$) with 100 µL final volume.

In step 4), after the modification of the DNA origami carrier with the lactosylated complementary oligonucleotide in step 3), 30 µL sample taken from the hybridization mixture, 10 µL of 2 mM doxorubicin solution and 160 µL of the TAE/Mg$^{2+}$ buffer are incubated at room temperature for 24 hours with shaking for doxorubicin intercalation. Doxorubicin intercalation mixture is then centrifuged at 10,000 rpm for 20 minutes at room temperature and doxorubicin loaded DNA origami carrier is obtained as a red pellet in centrifuge tube.

BRIEF DESCRIPTION OF THE DRAWINGS

A preparation method for the modified DNA origami based carrier developed to fulfill the objective of the present invention is illustrated in the accompanying Figures, wherein.

DETAILED DESCRIPTION OF THE EMBODIMENTS

A preparation method for the modified DNA origami based carrier developed to fulfill the objective of the invention comprises the following steps:
preparing DNA origami based carrier;
mixing complementary oligonucleotides in hybridization buffer;
incubating in a water bath at 95° C.;
slowly cooling from 95° C. to room temperature;
characterizing hybridized DNA origami carrier;
synthesizing lactose modified oligonucleotide;
mixing lactose, 5'-aminohexyloligonucleotide and sodium cyanoborohydride in borate buffer (pH 8, 0.1 M);
stirring the mixture at room temperature for 12 hours;
centrifuging the mixture to remove unreacted chemicals;
hybridizing lactose modified oligonucleotide to the DNA origami carrier;
mixing DNA origami structure and lactosylated oligonucleotide in hybridization buffer at room temperature for 18 hours;
intercalating the doxorubicin into DNA origami based carrier;
mixing DNA origami based carrier and doxorubicin in hybridization buffer;
stirring the mixture at room temperature for 24 hours;
centrifuging the mixture to collect the DNA origami-doxorubicin pellet.

In the inventive method, first DNA origami structures, tile shaped, was prepared by incubating nine complementary oligonucleotides (SEQ ID NOS: 1-9) in hybridization buffer solution applying slowly cooling method. The oligonucleotides complementary to the stick ends of the DNA origami (FIG. 10) are modified with lactose molecule. The newly prepared DNA origami carrier was hybridized from the sticky ends to the complementary oligonucleotide-lactose adjuncts. The chemotherapy drug, doxorubicin, was intercalated to the modified DNA origami structure stirring overnight at room temperature.

Figure 1:
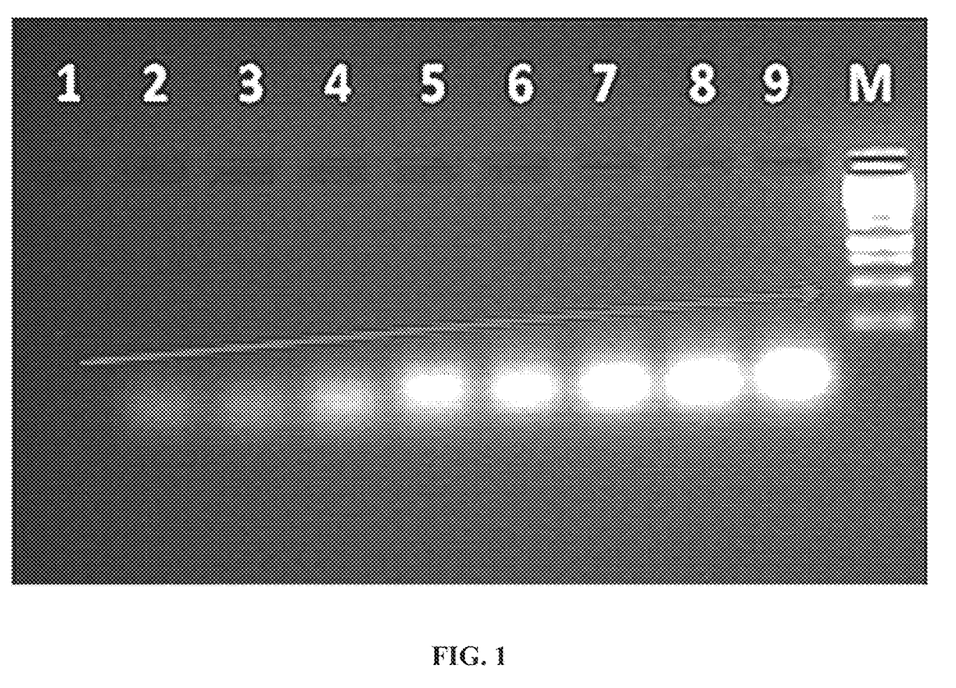
FIG. 1 is the agarose gel electrophoresis image of DNA tile formation obtained.

FIG. 1 shows the agarose gel electrophoresis image DNA origami formation. After the addition of each oligonucleotide and heating/cooling step, sample was taken from the hybridization solution and loaded into the gel to monitor the size change. On the agarose gel electrophoresis image of the hybridization samples, the line 1 shows the hybridization mixture containing only one oligonucleotide (oligonucleotide 1 as shown in SEQ ID NO: 1). The line 2 belongs to the hybridization mixture containing two oligonucleotides (oligonucleotide 1 as shown in SEQ ID NO: 1 and oligonucleotide 2 as shown in SEQ ID NO: 2). The line 3 represents the hybridization mixture containing three oligonucleotides (oligonucleotide 1 as shown in SEQ ID NO: 1, oligonucleotide 2 as shown in SEQ ID NO: 2 and oligonucleotide 3 as shown in SEQ ID NO: 3) and the finally line 9 is the sample of hybridization mixture of nine oligonucleotides (SEQ ID NOS: 1-9), which are necessary to form complete DNA tile structure. M represents the DNA ladder. When the oligonucleotides forming DNA tile are added sequentially into the hybridization buffer and the molecular weights of the DNA constructs increase, the bands (from line 1 to line 9) in the agarose gel migrates slower. The increase of the molecular weights of the DNA constructs as observed from the bands on the agarose gel electrophoresis image confirms the hybridization of oligonucleotides step by step to form DNA tile structure.

Figure 2A:
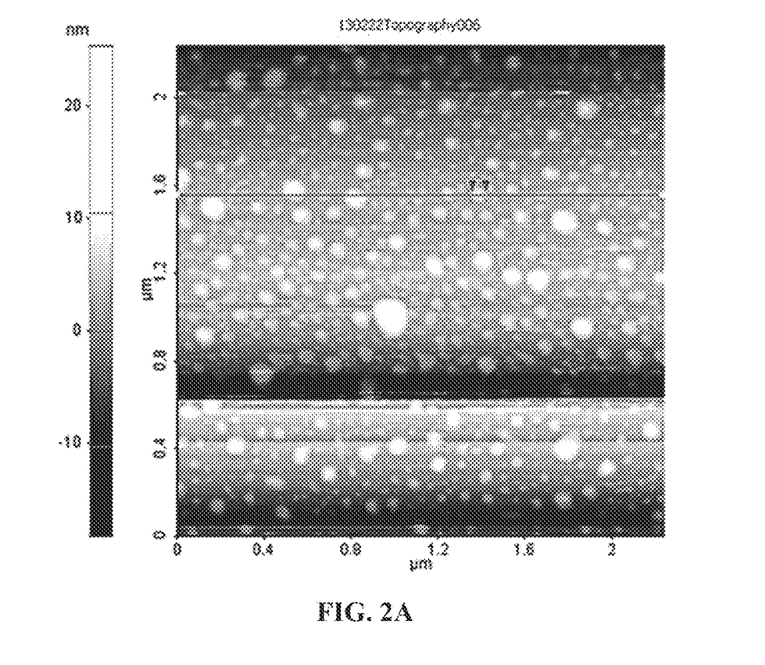
FIG. 2 is the AFM image of DNA tiles on a representative area on mica surface.
Figure 2B:
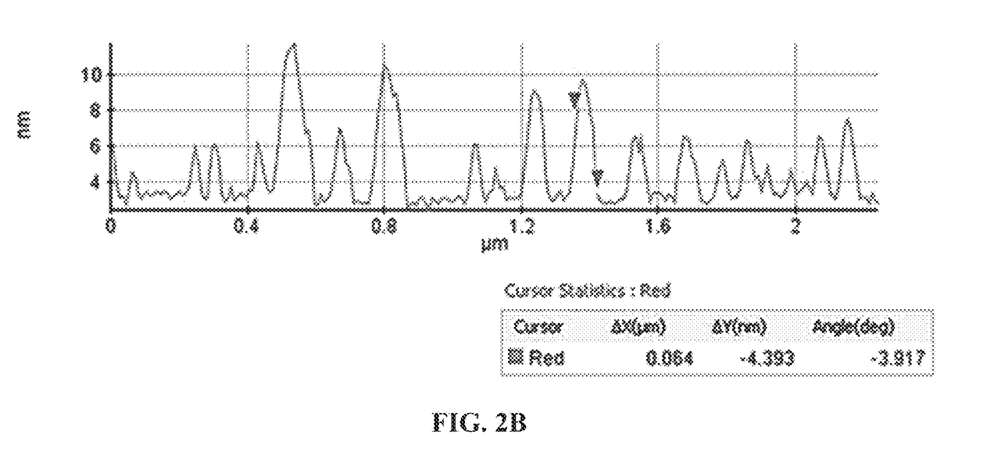

FIG. 2 shows the atomic force microscopy (AFM) image of DNA origami structure. The DNA tile samples taken from the hybridization media were dropped on mica surface for deposition and subsequently washed with deionized water. When the dropped DNA samples on mica were dried, images acquired at non-contact mode. Considering the distance between the base pairs in the DNA as 0.34 nm and the number of the base pairs in the DNA tile structure from one end to another, which is 40, the theoretical length of an assembled DNA tile can be estimated as 40 nm. A representative AFM image obtained from the DNA tile containing dried droplet area is shown on FIG. 2. On the right hand side of the image, the graph shows the image of one structure on the surface as marked with the red arrows. The marked structure is measured as 64 nm, which is larger than the theoretical value of 40 nm. However, as seen on the image, there are smaller and larger structures than the theoretical value. Considering the fact that the formation of DNA based structures is not always 100 percent efficient, this deviation can be acceptable. In conclusion, the analysis of the AFM image supports the DNA origami formation as combined with the gel electrophoresis results.

Figure 3:
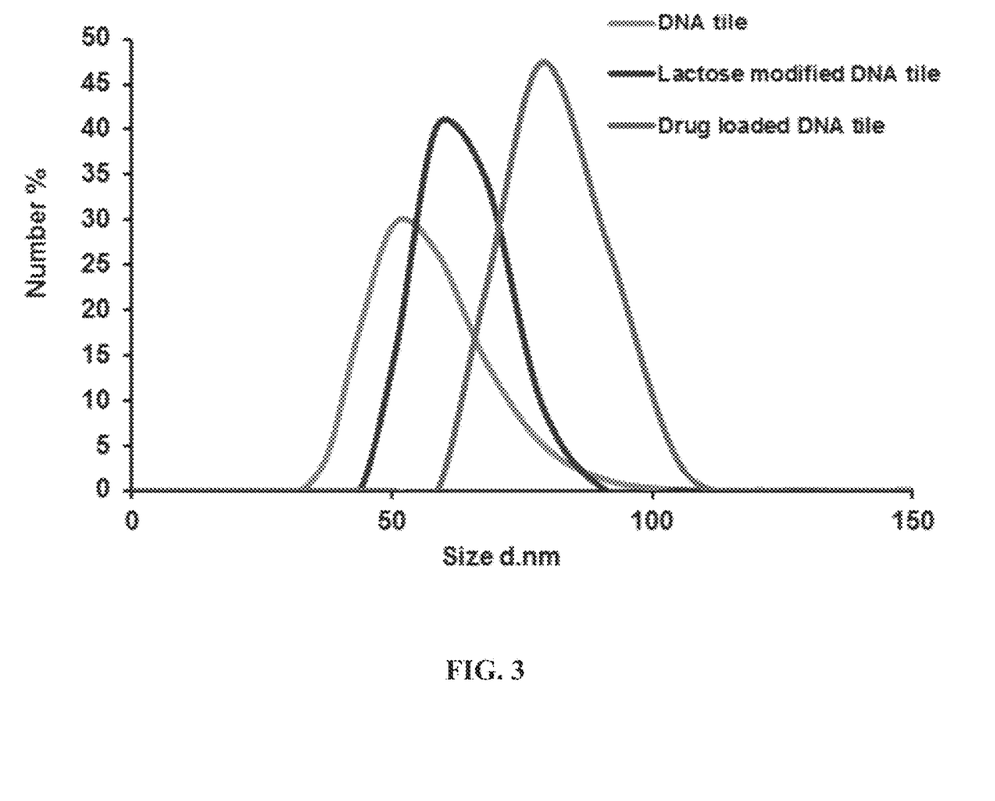
FIG. 3 is the dynamic light scattering analysis results of the DNA origami carrier.

FIG. 3 shows the hydrodynamic sizes of the DNA origami, doxorubicin loaded DNA origami, and lactose modified doxorubicin loaded DNA origami structures obtained with dynamic light scattering analysis. For DLS measurements, DNA tiles are dispersed in water. In water, DNA tiles are solvated by water molecules. This hydration layer causes grater diameter than theoretical size of the structure. Hydrodynamic size of DNA tiles was determined as approximately 50 nm, which is in good agreement with AFM results. The averaged size of lactose modified DNA tiles and doxorubicin loaded DNA tile structures was measured as approximately 60 nm and 78 nm, respectively.

Figure 4A:
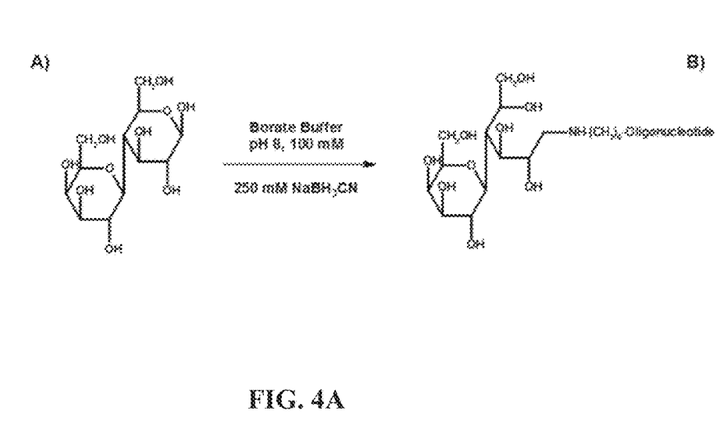
FIG. 4 is the lactose modification of 5'-NH$_2$-Oligonucleotide (A) and agarose gel electrophoresis image of lactose modification reaction sample and pure oligonucleotide (B).
Figure 4B:
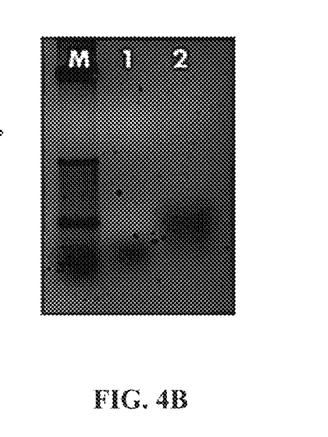

FIG. 4 shows the lactose modification of complementary 5'-$NH_2$-oligonucleotide (A) and agarose gel electrophoresis image of lactose modification reaction sample and pure oligonucleotide. The lactose modified oligonucleotides were synthesized with reductive amination as described in Maruyama et al., Lactose molecule was directly ligated to the 5' and 3' amino modified oligonucleotides in borate buffer (pH 8, 0.1 M) using same procedure. Samples taken from the reaction mixtures were carried out in 2% agarose gel. On the agarose gel electrophoresis image, M represents the DNA ladder; the line 1 represents the pure oligonucleotide (without modification), line 2 belongs to the lactose-modified oligonucleotide. With the attachment of lactose molecule to the oligonucleotide structure, a slower migration was observed a result of increased molecular weight the conjugate.

Figure 5:
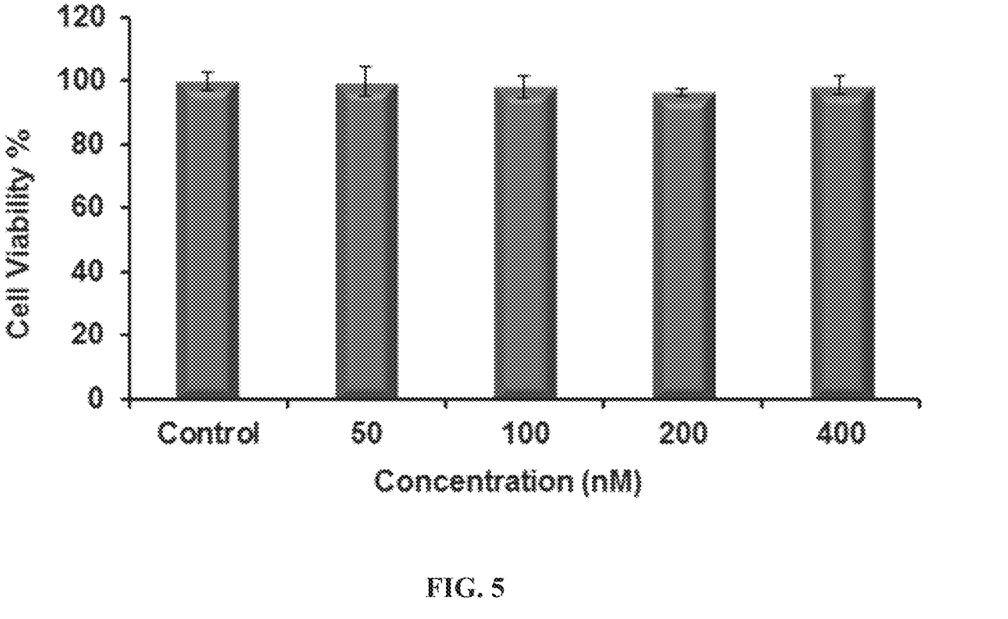
FIG. 5 is the cytotoxicity comparison of the DNA tile structure with/without lactose modification on MDA-MB-231 cells.

FIG. 5 shows the cytotoxicity of the DNA origami carrier. The cytotoxicity assessments of the DNA origami structure were carried out on MDA-MB-231 cell line at a concentration range of 50-400 nM. According to the cell viability results of the experiment, the DNA-tiles are non-toxic to the cells.

Figure 6:
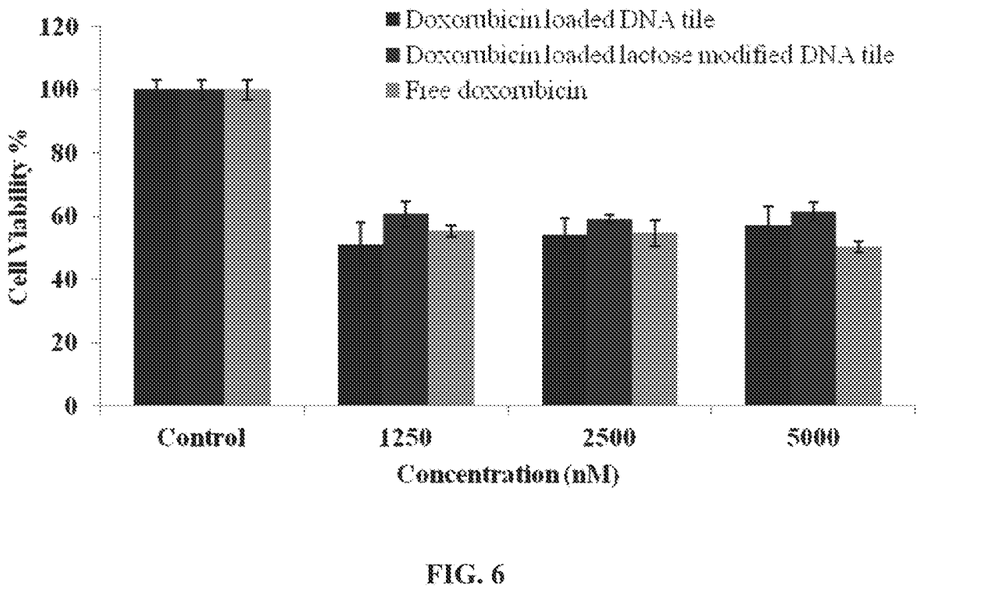
FIG. 6 is the cytotoxicity of the doxorubicin loaded DNA origami carrier with/without lactose modification.

FIG. 6 shows the cytotoxicity of free doxorubicin, doxorubicin loaded DNA origami carrier and the lactose modified-doxorubicin loaded DNA origami carrier. a slight improvement with lactose modified DNA tiles was observed on cell viability and incorporation of doxorubicin into the DNA origami with/without lactose modification does not significantly reduce the cellular cytotoxicity. This indicated that the effect of doxorubicin remains intact.

Figure 7:
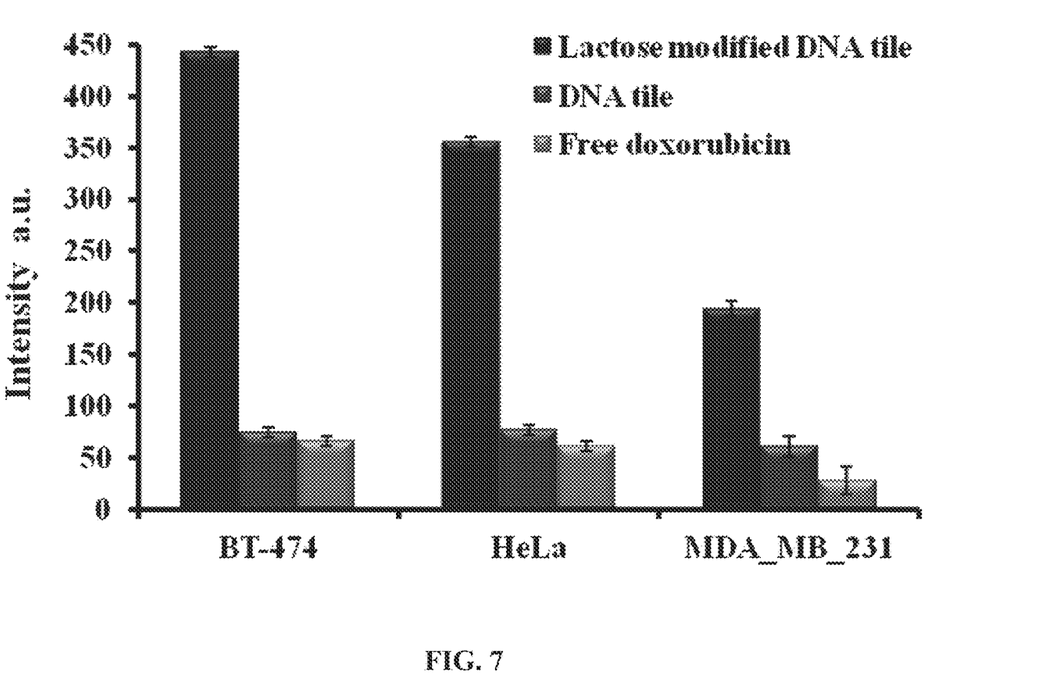
FIG. 7 is the intracellular uptake of DNA origami based carrier with/without lactose modification.

FIG. 7 shows the intracellular uptake of doxorubicin content, which determined quantitatively by using fluorescence spectroscopy. According to the FIG. 7, when the fluorescence intensities are compared, the free doxorubicin and doxorubicin loaded DNA origami based carrier with/without lactose modification, the lactose modified DNA origami based carrier showed the highest intensity. Results suggest that more doxorubicin taken into the cells, when the cancer cells were treated with lactose modified DNA origami based carrier.

Figure 8:
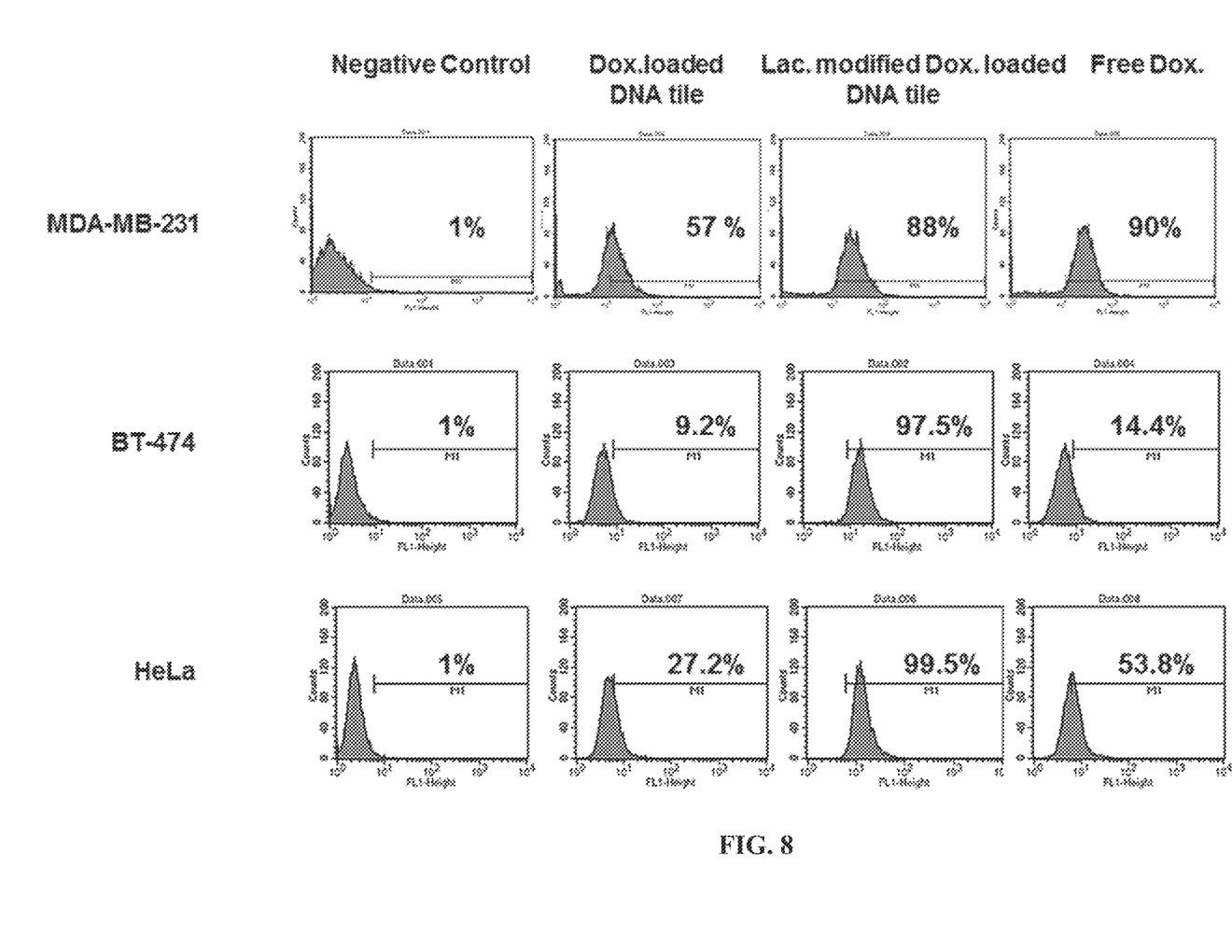
FIG. 8 is the flow cytometry graphs of BT-474, HeLa and MDA-MB-231 cancer cells incubated with free doxorubicin and DNA origami based carrier with/without lactose modification.

FIG. 8 shows the flow cytometry results of the cancer cells incubated with free doxorubicin, doxorubicin loaded DNA origami based carrier with/without lactose modification. According to the flow cytometry results, lactose modification increases the number of cells internalized the DNA origami based carrier indicating faster entrance of the lactose modified DNA origami structures into the cells. It was observed that the lactose-modified doxorubicin loaded DNA origami based carriers are internalized by the each cancer cells more than those of the unmodified DNA origami based carrier.

Figure 9:
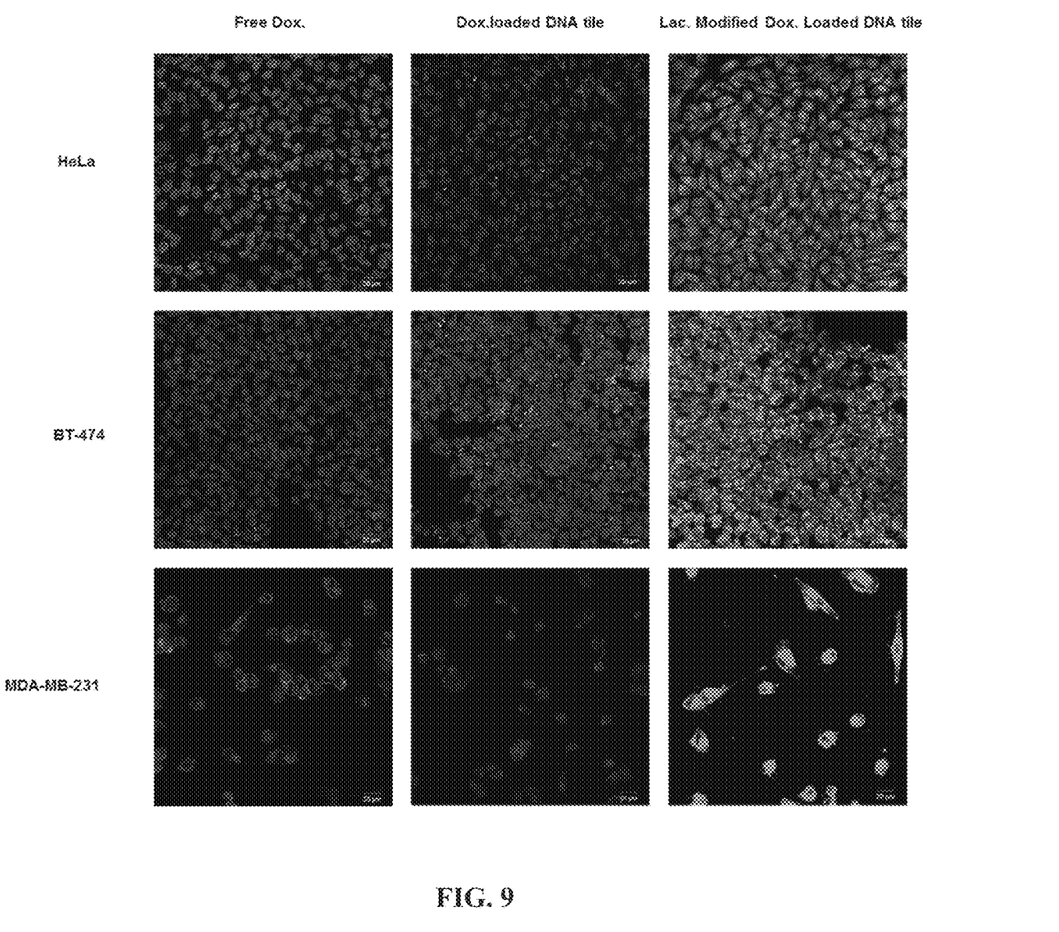
FIG. 9 is the confocal microscopy images of the cancer cells incubated with free doxorubicin, doxorubicin loaded DNA tile and lactose modified DNA origami based carrier.

FIG. 9 shows the localization of free doxorubicin and doxorubicin loaded-DNA origami based carrier with/without lactose modification monitored with confocal microscopy. According to the images, the fluorescence intensity from the cells exposed to the lactose modified and doxorubicin loaded DNA origami based carrier was higher (brighter) under the same experimental conditions indicating the faster uptake of the lactose modified DNA origami based carrier.

FIG. 10 shows the proposed structure and binding points of the oligonucleotide modified agents. A multifunctional DNA based nanocarrier system can be constructed by maintaining the basic origami tile structure and attaching the mentioned molecules to the oligonucleotides complementary to the sticky ends of the DNA origami structure. DNA origami (FIG. 10) are modified with lactose molecule. The newly prepared DNA origami carrier was hybridized from the sticky ends to the complementary oligonucleotide-lactose adjuncts.

What is claimed is:

1. A preparation method for a DNA origami based carrier, comprising the following steps:
   preparing a first DNA origami based carrier, comprising the following steps:
       mixing complementary oligonucleotides in a first hybridization buffer to obtain a first hybridization mixture;
       incubating the first hybridization mixture in a water bath at 95° C. to obtain a second hybridization mixture;
       slowly cooling the second hybridization mixture from 95° C. to room temperature to obtain a first DNA origami based carrier; and
       characterizing the first DNA origami based carrier to obtain a molecular weight and a size of the first DNA origami based carrier;
   synthesizing a lactose modified oligonucleotide, comprising the following steps:
       mixing a lactose, a 5'-aminohexyloligonucleotide and a sodium cyanoborohydride in a borate buffer (pH 8) to obtain a first mixture;
       stirring the first mixture at a room temperature for 12 hours to obtain a second mixture; and
       centrifuging the second mixture to remove unreacted chemicals to obtain the lactose modified oligonucleotide;
   hybridizing the lactose modified oligonucleotide to the first DNA origami based carrier, comprising a step of:
       mixing the first DNA origami based carrier and the lactose modified oligonucleotide in a second hybridization buffer at room temperature for 18 hours to obtain a second DNA origami carrier; and
   intercalating a doxorubicin into the second DNA origami based carrier, comprising t following steps:
       mixing the second DNA origami based carrier and the doxorubicin in a third hybridization buffer to obtain a third mixture;
       stirring the third mixture at room temperature for 24 hours to obtain a doxorubicin intercalation mixture; and
       centrifuging the doxorubicin intercalation mixture to collect a third DNA origami based carrier, wherein the third DNA origami based carrier is loaded with doxorubicin.

2. The preparation method for the DNA origami based carrier according to claim 1, wherein 2 µL of each complementary oligonucleotides, from a 100 µM stock, are added into the first hybridization buffer to obtain the first hybridization mixture and the final volume of the first hybridization mixture is completed to 200 µL, wherein the first hybridization buffer is a TAE/Mg$^{2+}$ buffer.

3. The preparation method for the DNA origami based carrier according to claim 2, wherein the first DNA origami based carrier is characterized by using atomic force microscopy (AFM), agarose gel electrophoresis and dynamic light scattering analysis.

4. The preparation method for the DNA origami based carrier according to claim 3, wherein the lactose in a 20 mM solution, the 5'aminohexyloligonucleotide in a 50 µM solution and 250 mM sodium cyanoborohydride are added into a 0.1 M borate buffer a pH8 to obtain the first mixture and the first mixture is further incubated for 12 hours 60° C.; and the second mixture is transferred into an ultracentrifuge column with 3000 MWCO and centrifuged for 45 minutes at 3800 rpm to remove the unreacted chemicals to obtain the lactose modified oligonucleotide.

5. The preparation method for the DNA origami based carrier according to claim 4, wherein the lactose modified oligonucleotide is hybridized into the first DNA origami based carrier by incubating 10 µL of the lactose modified oligonucleotide and 30 µL of the first DNA origami based carrier at room temperature for 18 hours in the second hybridization buffer with a 100 µL final volume to obtain the second DNA origami based carrier, wherein the second hybridization buffer is a TAE/Mg$^{2+}$ buffer.

6. The preparation method for the DNA origami based carrier according to claim 5, wherein after the second DNA origami based carrier is obtained, 30 µL of the second DNA origami based carrier, 10 µL of a 2 mM doxorubicin solution and 160 µL of the third hybridization buffer are incubated at room temperature for 24 hours with shaking for a doxorubicin intercalation to obtain the doxorubicin intercalation mixture, wherein the third hybridization buffer is a TAE/Mg$^{2+}$ buffer.

7. The preparation method for the DNA origami based carrier according to claim 6, wherein the doxorubicin intercalation mixture is centrifuged at 10000 rpm for 20 minutes at room temperature and the third DNA origami based carrier is obtained, wherein the third DNA origami based carrier is a red pellet in a centrifuge tube.

* * * * *